United States Patent
Xia et al.

(10) Patent No.: US 10,220,096 B2
(45) Date of Patent: Mar. 5, 2019

(54) INJECTABLE AND STABLE HYDROGELS WITH DYNAMIC PROPERTIES MODULATED BY BIOCOMPATIBLE CATALYSTS

(71) Applicant: The Board of Trustees of the Leland Stanford Junior University, Stanford, CA (US)

(72) Inventors: Yan Xia, Stanford, CA (US); Junzhe Lou, Stanford, CA (US); Ovijit Chaudhuri, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/782,612

(22) Filed: Oct. 12, 2017

(65) Prior Publication Data
US 2018/0104348 A1 Apr. 19, 2018

Related U.S. Application Data

(60) Provisional application No. 62/407,939, filed on Oct. 13, 2016.

(51) Int. Cl.
| | | |
|---|---|---|
| A61K 47/36 | (2006.01) | |
| A61K 9/00 | (2006.01) | |
| A61K 9/06 | (2006.01) | |
| C08L 5/08 | (2006.01) | |
| A61K 9/50 | (2006.01) | |
| A61K 35/51 | (2015.01) | |

(52) U.S. Cl.
CPC .......... *A61K 47/36* (2013.01); *A61K 9/0019* (2013.01); *A61K 9/06* (2013.01); *A61K 9/5036* (2013.01); *A61K 35/51* (2013.01); *C08L 5/08* (2013.01); *C08L 2203/02* (2013.01); *C08L 2205/025* (2013.01)

(58) Field of Classification Search
None
See application file for complete search history.

(56) References Cited

U.S. PATENT DOCUMENTS

2002/0131952 A1* 9/2002 Hennink ............. A61K 9/1652
424/78.37
2014/0105960 A1* 4/2014 Zoldan ................ A61K 9/0024
424/450

FOREIGN PATENT DOCUMENTS

WO WO-2013114115 A1 * 8/2013 ........... C07D 209/10

OTHER PUBLICATIONS

T Ito, Y Yeo, CB Highley, E Bellas, DS Kohane. "Dextran-based in situ cross-linked injectable hydrogels to prevent peritoneal adhesions." Biomaterials, vol. 28, 2007, pp. 3418-3426. (Year: 2007).*

(Continued)

*Primary Examiner* — Isaac Shomer
(74) *Attorney, Agent, or Firm* — Foley & Lardner LLP; Cliff Z. Liu

(57) ABSTRACT

A hydrogel composition includes: (1) a polymer network including a first water-soluble polymer and a second water-soluble polymer that are crosslinked through dynamic bonds; and (2) a catalyst to modulate a rate of exchange of crosslinking of the polymer network.

16 Claims, 10 Drawing Sheets

(56) References Cited

OTHER PUBLICATIONS

H Epstein-Barash, G Orbey, BE Polat, RH Ewoldt, J Feshitan, R Langer, MA Borden, DS Kohane. "A microcomposite hydrogel for repeated on-demand ultrasound-triggered drug delivery." Biomaterials, vol. 31, 2010, pp. 5208-5217. (Year: 2010).*
D Larsen, M Pittelkow, S Karmakar, ET Kool. "New Organocatalyst Scaffolds with High Activity in Promoting Hydrazone and Oxime Formation at Neutral pH." Organic Letters, vol. 17, pp. 274-277, published Dec. 29, 2014. (Year: 2014).*
Aguado, B.A. et al. (2012) "Improving Viability of Stem Cells During Syringe Needle Flow Through the Design of Hydrogel Cell Carriers," Tissue Eng. Part A 18(7-8):806-815.
Appel, E.A. et al. (2012) "Supramolecular polymeric hydrogels," Chem. Soc. Rev. 41:6195-6214.
Cai, L. et al. (2015) "Injectable Hydrogels with In Situ Double Network Formation Enhance Retention of Transplanted Stem Cells," Adv. Funct. Mater. 25(9):1344-1351.
Chung, H.J. et al. (2009) "Self-assembled and nanostructured hydrogels for drug delivery and tissue engineering," Nano Today 4(5):429-437.
Dooling, L.J. et al. (2016) "Programming Molecular Association and Viscoelastic Behavior in Protein Networks," Adv. Mater. 28:4651-4657.
Glassman, M.J. et al. (2013) "Self-Assembly: Reinforcement of Shear Thinning Protein Hydrogels by Responsive Block Copolymer Self-Assembly," Adv. Funct. Mater. 23(9):1182-1193.
Guvendiren, M. et al. (2012) "Shear-thinning hydrogels for biomedical applications," Soft Matter 8:260-272.
Haines-Butterick, L. et al. (2007) "Controlling hydrogelation kinetics by peptide design for three-dimensional encapsulation and injectable delivery of cells," Proc. Natl. Acad. Sci. USA 104(19):7791-7796.
Jeong, B. et al. (1997) "Biodegradable block copolymers as injectable drug-delivery systems," Nature 388:860-862.
Lu, H.D. et al. (2012) "Injectable shear-thinning hydrogels engineered with a self-assembling Dock-and-Lock mechanism," Biomaterials 33(7):2145-2153.
Lu, H.D. et al. (2013) "Secondary Photocrosslinking of Injectable Shear-Thinning Dock-and-Lock Hydrogels," Adv. Healthcare Mater. 2(7):1028-1036.
Olsen, B.D. et al. (2010) "Yielding Behavior in Injectable Hydrogels from Telechelic Proteins," Macromolecules 43(21):9094-9099.
Rodell, C.B. et al. (2015) "Shear-Thinning Supramolecular Hydrogels with Secondary Autonomous Covalent Crosslinking to Modulate Viscoelastic Properties In Vivo," Adv. Funct. Mater. 25(4):636-644.
Rodell, C.B. et al. (2016) "Injectable and Cytocompatible Tough Double-Network Hydrogels through Tandem Supramolecular and Covalent Crosslinking," Adv. Mater. 28(38):8419-8424.
Rosales, A.M. et al. (2016) "The design of reversible hydrogels to capture extracellular matrix dynamics," Nat. Rev. Mater. 1:15012.
Tseng, T-C. et al. (2015) "An Injectable, Self-Healing Hydrogel to Repair the Central Nervous System," Adv. Mater. 27:3518-3524.
Wang, H. et al. (2015) "Adaptable Hydrogels: Adaptable Hydrogel Networks with Reversible Linkages for Tissue Engineering," Adv. Mater. 27(25):3717-3736.
Wang, H. et al. (2017) "Hydrogels: Covalently Adaptable Elastin-Like Protein-Hyaluronic Acid (ELP-HA) Hybrid Hydrogels with Secondary Thermoresponsive Crosslinking for Injectable Stem Cell Delivery," Adv. Funct. Mater. 27(28).
Yan, C. et al. (2010) "Injectable solid hydrogel: mechanism of shear-thinning and immediate recovery of injectable beta-hairpin peptide hydrogels," Soft Matter 6(20):5143-5156.
Yan, C. et al. (2012) "Injectable Solid Peptide Hydrogel as a Cell Carrier: Effects of Shear Flow on Hydrogels and Cell Payload," Langmuir 28(14):6076-6087.
Yang, J-A. et al. (2014) "In situ-forming injectable hydrogels for regenerative medicine," Prog. Polym. Sci. 39(12):1973-1986.
Yesilyurt, V. et al. (2015) "Injectable Self-Healing Glucose-Responsive Hydrogels with pH-Regulated Mechanical Properties," Adv. Mater. 28(1):86-91.

* cited by examiner

INJECTABLE AND STABLE HYDROGELS WITH DYNAMIC PROPERTIES MODULATED BY BIOCOMPATIBLE CATALYSTS

CROSS-REFERENCE TO RELATED APPLICATION

This application claims the benefit of U.S. Provisional Application No. 62/407,939, filed Oct. 13, 2016, the contents of which are incorporated herein by reference in their entirety.

BACKGROUND

Hydrogels are desired for use in biomedical applications such as tissue engineering and drug delivery due to their high water content and generally favorable biocompatibility. Injectable hydrogels that encapsulate bioactive therapeutics and cells have gained growing interest because they can be administered via straightforward and minimally invasive procedures and used for cell transplantation and three-dimensional (3D) printing of cell cultures. These hydrogels can deliver cells at a target site through a rapid sol-gel transition, and also can provide a 3D scaffold to support cell viability post-injection.

It is against this background that a need arose to develop embodiments of this disclosure.

SUMMARY

Hydrogels are desirable materials for biomedical applications, such as cell scaffolds for tissue regeneration and 3D printing of cell cultures as well as delivery materials for therapeutic cell transplantation and drug delivery for disease treatment. Injectable and biocompatible hydrogels are desired for cell transplantation to provide mechanical protection of cells during injection and a stable scaffold for cell adhesion post-injection. Injectable hydrogels should be readily pushed through a syringe needle and quickly recover to a gel state, thus generally specifying noncovalent or dynamic crosslinking. However, a dilemma can be present in the design of dynamic hydrogels: hydrogels with fast exchange of crosslinks are more readily ejected using less force, but lack long-term stability; in contrast, slow exchange of crosslinks improves stability, but compromises injectability and thus the ability to protect cells under flow. Some embodiments resolve this dilemma using biocompatible catalysts to modulate the dynamic properties of hydrogels at different time points of application to have both high injectability and high stability. In some embodiments, a hyaluronic acid (HA)-based hydrogel is formed through dynamic covalent hydrazone crosslinking in the presence of a biocompatible organic catalyst. The catalyst accelerates the formation and exchange of hydrazone bonds, enhancing injectability, but rapidly diffuses away from the hydrogel after injection to retard the exchange and improve the long-term stability for cell culture.

In some embodiments, a hydrogel composition includes: (1) a polymer network including a first water-soluble polymer and a second water-soluble polymer that are crosslinked through dynamic bonds; and (2) a catalyst to modulate a rate of exchange of crosslinking of the polymer network.

In some embodiments of the hydrogel composition, the first water-soluble polymer and the second water-soluble polymer are crosslinked through hydrazone bonds.

In some embodiments of the hydrogel composition, the first water-soluble polymer is modified with a hydrazine or hydrazide functional group, and the second water-soluble polymer is modified with an aldehyde functional group.

In some embodiments of the hydrogel composition, the first water-soluble polymer and the second water-soluble polymer are selected from polysaccharides and proteins.

In some embodiments of the hydrogel composition, at least one of the first water-soluble polymer or the second water-soluble polymer is hyaluronic acid.

In some embodiments of the hydrogel composition, the first water-soluble polymer is hyaluronic acid modified with a hydrazine or hydrazide functional group, and the second water-soluble polymer is hyaluronic acid modified with an aldehyde functional group.

In some embodiments of the hydrogel composition, the catalyst includes an acidic functional group, a basic functional group, or both.

In some embodiments of the hydrogel composition, the catalyst is a small molecule organic compound.

In some embodiments of the hydrogel composition, the catalyst is a heterocyclic aromatic compound.

In some embodiments of the hydrogel composition, the catalyst is an N-heterocyclic aromatic compound substituted with an amino-containing group and a sulfonyl hydroxide-containing group. For example, the catalyst can be an aminoalkyl-substituted and alkyl sulfonyl hydroxide-substituted N-heterocyclic aromatic compound.

In some embodiments of the hydrogel composition, a concentration of the catalyst in the hydrogel composition is in a range from about 0.5 mM to about 500 mM.

In some embodiments of the hydrogel composition, a content of the polymer network in the hydrogel composition is in a range from about 0.5 wt. % to about 30 wt. %.

In additional embodiments, a method of using the hydrogel composition of any of the foregoing embodiments includes: (1) encapsulating cells in the polymer network of the hydrogel composition; and (2) injecting the hydrogel composition into a subject. In some embodiments of the method, injecting the hydrogel composition is performed using a syringe. In some embodiments of the method, the subject is a mammal, such as a human.

In additional embodiments, a method of forming a hydrogel composition includes: (1) providing a first water-soluble polymer, a second water-soluble polymer, and a catalyst; and (2) combining the first water-soluble polymer, the second water-soluble polymer, and the catalyst in a liquid medium including water to form the hydrogel composition. The first water-soluble polymer is modified with a hydrazine or hydrazide functional group, and the second water-soluble polymer is modified with an aldehyde functional group. The first water-soluble polymer are the second water-soluble polymer are crosslinked through hydrazone bonds to form a polymer network, and a rate of exchange of crosslinking of the polymer network is modulated by the catalyst.

In some embodiments of the method, the first water-soluble polymer and the second water-soluble polymer are selected from polysaccharides and proteins.

In some embodiments of the method, at least one of the first water-soluble polymer or the second water-soluble polymer is hyaluronic acid.

In some embodiments of the method, the catalyst is a heterocyclic aromatic compound.

In some embodiments of the method, the catalyst is an N-heterocyclic aromatic compound substituted with an amino-containing group and a sulfonyl hydroxide-containing group. For example, the catalyst can be an aminoalkyl-substituted and alkyl sulfonyl hydroxide-substituted N-heterocyclic aromatic compound.

In some embodiments of the method, the catalyst is zwitterionic.

Other aspects and embodiments of this disclosure are also contemplated. The foregoing summary and the following detailed description are not meant to restrict this disclosure to any particular embodiment but are merely meant to describe some embodiments of this disclosure.

BRIEF DESCRIPTION OF THE DRAWINGS

For a better understanding of the nature and objects of some embodiments of this disclosure, reference should be made to the following detailed description taken in conjunction with the accompanying drawings.

DESCRIPTION

Figure 1:
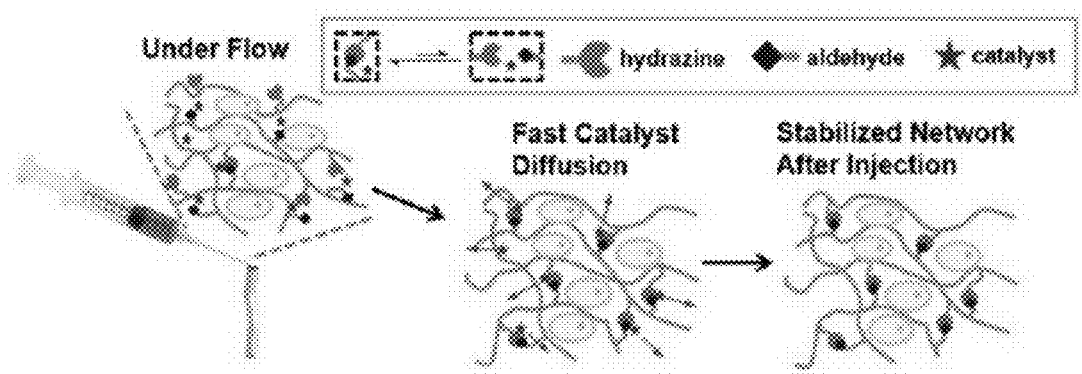
FIG. 1. Schematic representation of using diffusible organic catalyst to temporally modulate dynamic properties of hydrazone-crosslinking hydrogels. During injection, the incorporated catalyst promotes rapid exchange of hydrazone crosslinks and rearrangement of a network to facilitate flow. After injection, the catalyst rapidly diffuses away to slow down hydrazone exchange, resulting in the unchanged structure of the network with improved stability.

Shear-thinning and self-healing hydrogels encompass a class of injectable materials which exhibit viscous flow under an applied shear stress and time-dependent recovery upon removing the stress. These hydrogels can be prepared ex vivo with cells and therapeutics encapsulated, and then flow through a needle under force and recover its modulus at the target site. Such injectable properties specify the hydrogels to be noncovalently or dynamically crosslinked, such as peptide self-assembly, electrostatic attraction, hydrogen bonding, supramolecular complexation, protein interactions, and dynamic chemical bonds. Additional, injectable hydrogels can provide cyto-protection attributed to a shear-banding mechanism to mitigate against damage of cell membranes. The shear-banding and plug-flow profiles localize a shear deformation within narrow regions close to a needle wall, therefore shielding most cells from extensional and shear flow. Relatively weak physical interactions and dynamic bonds with fast exchange kinetics facilitate injection of a gel, but can lead to rapid erosion of the gel. The lack of long-term stability post-injection constrains biological applications of such hydrogels to provide cell scaffolding or prolonged drug release. In the pursuit of an injectable and stable composition, dual-crosslinked hydrogels include an additional crosslinking stage post-injection. A first network is weakly crosslinked ex vivo via noncovalent interactions, and a second crosslinking is implemented in situ using ultraviolet (UV) irradiation, temperature, or pH variation to improve mechanical properties and stability of the hydrogels. The dual-crosslinking design can increase material stability, but the secondary crosslinking stage can involve non-physiological conditions and can vary network structures and mechanical properties of hydrogels, which can be incompatible with biomedical applications.

For injectable hydrogels, it is desired that the exchange dynamics of crosslinking of the hydrogels is modulated at different time points under physiological conditions without altering an equilibrium network structure, chemical composition, or scaffold stiffness. That is, rapid crosslink exchange during injection to reduce cell damage, but slow crosslink exchange post-injection to enhance long-term network stability. Some embodiments of this disclosure are directed to an improved approach to achieve this goal by temporally modulating the exchange dynamics of hydrazone crosslinking using an incorporated biocompatible, organic catalyst under physiological conditions, without changing a network structure or scaffold modulus. The catalyst accelerates both the formation and exchange of hydrazone bonds to facilitate gel shear-thinning and injectability, but quickly diffuses out of a hydrogel after injection, leading to much slower bond exchange to stabilize a matrix. Since a catalyst accelerates the rate of bond exchange but does not affect the thermodynamic equilibrium, the network structure remains unchanged.

FIG. 1 illustrates a biocompatible hydrogel composition that is injectable, and has tunable mechanical properties. Stress relaxation of a hydrogel is modulated by including a small molecule, biocompatible, organic catalyst (or organocatalyst) in the composition. The biocompatible organic catalyst is used to modulate the dynamic exchange of crosslinking of the hydrogel to tune its stress relaxation rate and render it injectable. After injection of the hydrogel encapsulating cells, the catalyst rapidly diffuses out of the hydrogel to slow down the exchange of crosslinking to stabilize the hydrogel. The catalyst does not change a structure of the hydrogel but modulates the dynamics of its crosslinking. Thus, the catalyst allows temporal control of the hydrogel's mechanical properties to switch from fast stress relaxation for injectability to slow stress relaxation for long-term stability, depending on the presence of catalyst. Further, a modulus and a stress-relaxation rate can be independently tuned by parameters such as polymer concentration and catalyst concentration.

Some embodiments of this disclosure are directed to compositions including water-soluble polymer-based viscoelastic hydrogels that exhibit viscous flow under shear stress and time-dependent recovery upon relaxation under physiological conditions, such as at or about room temperature (about 20 to about 40° C.) and a pH of about 6 to about 8. In some embodiments, these hydrogels are formed through dynamic bonds, such as covalent hydrazone bonds resulting from hydrazine (or hydrazide) and aldehyde functional groups of water-soluble polymers.

In some embodiments, a hydrogel includes a crosslinked polymer network that is formed from water-soluble polymers including associative functional groups. In forming the network, the polymers interact with one another through their associative functional groups to form the network. An associative functional group of one polymer interacts with an associative functional group of another polymer to provide intermolecular bonds or links between the polymers. In a crosslinked polymer network of some embodiments, polymers interact with one another (through their associative functional groups) by reversible or dynamic covalent bonds.

By crosslinking through reversible or dynamic covalent bonds, a polymer network provides a self-healing function via these bonds, which can break preferentially (instead of other covalent bonds) during a mechanical damage event. These 'broken' bonds can dynamically associate and dissociate to provide self-recovery.

Hydrazone formation is an efficient, biocompatible chemistry that can be used for bioconjugation under physiological conditions. The reaction rate of formation and dissociation of a hydrazone bond can be dependent on structures of aldehyde and hydrazine (or hydrazide) used to form the hydrazone bond. Such dynamic nature makes hydrazone an appealing crosslinking chemistry to form viscoelastic hydrogels with tunable mechanical properties by structure variation. A variety of compounds can be used as catalysts to accelerate hydrazone formation, including acid/base catalysts in accelerating a rate-limiting dehydration stage. These catalysts can promote the rate of hydrazone exchange, thus enhancing the ability of hydrazone-crosslinking hydrogels to flow through a syringe One aspect of some embodiments of this disclosure is to provide hydrazine-modified, hydrazide-modified, and aldehyde-modified water-soluble polymer derivatives with biomedicine and other usages and which contain adjustable molecular structures (e.g., of side chains or backbone) to yield tunable mechanical properties. Another aspect of some embodiments of this disclosure is to provide hydrazone bond crosslinked hydrogels composed of hydrazine-modified (or hydrazide-modified) and aldehyde-modified polymer derivatives.

In some embodiments, water-soluble polymers, such as including side carboxyl groups, are used as starting materials, and hydrazine-modified, hydrazide-modified, and aldehyde-modified polymers are synthesized through chemical modification.

Modified polymers of some embodiments of this disclosure are represented by the following chemical structures (I), (II), and (III):

$$P\text{—}NH\text{—}NH_2 \tag{I}$$

$$P'\text{—}(C\text{=}O)\text{—}NH\text{—}NH_2 \tag{II}$$

$$P''\text{—}(C\text{=}O)\text{—}H \tag{III}$$

Chemical structure (I) represents a water-soluble polymer P that is modified with a moiety containing a nitrogen-nitrogen covalent bond and, more specifically, with a hydrazine functional group (—NH—NH$_2$). In general, the hydrazine functional group can be included in a side chain or as part of a backbone of the polymer P. Also, the polymer P can be modified with a single hydrazine functional group, or can be modified with multiple hydrazine functional groups.

Chemical structure (II) represents a water-soluble polymer P' that is modified with a moiety containing a nitrogen-nitrogen covalent bond and, more specifically, with a hydrazide functional group (—(C=O)—NH—NH$_2$). In general, the hydrazide functional group can be included in a side chain or as part of a backbone of the polymer P'. Also, the polymer P' can be modified with a single hydrazide functional group, or can be modified with multiple hydrazide functional groups.

Chemical structure (III) represents a water-soluble polymer P" that is modified with a carbonyl (C=O)-containing moiety and, more specifically, with an aldehyde functional group (—(C=O)—H). In general, the aldehyde functional group can be included in a side chain or as part of a backbone of the polymer P". Also, the polymer P" can be modified with a single aldehyde functional group, or can be modified with multiple aldehyde functional groups.

The polymers P, P', and P" in chemical structures (I), (II), and (III) can be the same or different, and can be selected from a range of water-soluble (or hydrophilic) polymers. Examples of suitable polymers include polysaccharides, such as chondroitin sulfate, dermatan, heparin, heparan, alginic acid, hyaluronic acid, dermatan sulfate, pectin, carboxymethyl cellulose, carboxymethyl chitosan, and their salts. Additional examples of suitable polymers include proteins, such as collagen protein, gelatin, elastin, decorin, laminin, fibronectin, and their salts. Further examples of suitable polymers include synthetic polymers, such as polyacrylic acid, polymethylacrylic acid, polyaspartic acid, polytartaric acid, polyglutamic acid, polyfumaric acid, poly(N-isopropylacrylamide), polyacrylamide, poly(2-oxazoline), polyethylenimine, polymethacrylate, and their salts.

For example, hyaluronic acid (HA) is an anionic glycosaminoglycan widely distributed in many tissues including cartilage and brain. Due to its biocompatibility and diverse biological functions, HA is a desirable polymer for the formation of hydrogels with desired morphology, mechanical properties, and bioactivity for biomedical applications.

In some embodiments, the polymers P, P', and P" can be modified by including hydrazine, hydrazide, and aldehyde functional groups in side chains of the polymers P, P', and P", in which case the modified polymers are represented by the following chemical structures (Ia), (IIa), and (IIIa):

P-L-NH—NH$_2$     (Ia)

P'-L'-(C=O)—NH—NH$_2$     (IIa)

P"-L"-(C=O)—H     (IIIa)

Linkers L, L', and L" in chemical structures (Ia), (IIa), and (IIIa) can be the same or different. In some embodiments, L, L', and L" can be, or can include, a $C_1$-$C_{20}$, $C_1$-$C_{15}$, $C_1$-$C_{10}$, $C_1$-$C_5$, $C_2$-$C_{15}$, $C_2$-$C_{10}$, or $C_2$-$C_5$ alkylene or heteroalkylene group, optionally substituted with 1-5 $C_1$-$C_6$ alkyl groups or other substituent groups. For example, L, L', and L" can be, or can include, —(CH$_2$)$_n$—, where n is from 1-20, 1-15, 1-10, 1-5, 2-15, 2-10, or 2-5. L, L', and L" also can be, or can include, one or more aromatic rings, such as benzene rings, and also can be, or can include, one or more heterocylic rings, such as triazole rings. L, L', and L" also can be, or can include, one or more amide linkages (—(C=O)—NR—), where R is hydrogen, a $C_1$-$C_6$ alkyl group, or another substituent group. In some embodiments, L, L', and L" can be, or can include, a polyether group, such as —[(CHR)$_x$O]$_y$-, where x is from 1-10, 1-5, 2-10, or 2-5, y is from 1-20, 1-15, 1-10, 1-5, 2-15, 2-10, or 2-5, and R is hydrogen, a $C_1$-$C_6$ alkyl group, or another substituent group.

For example, if the polymers P, P', and P" are hyaluronic acid, specific examples of the modified polymers of some embodiments include the following:

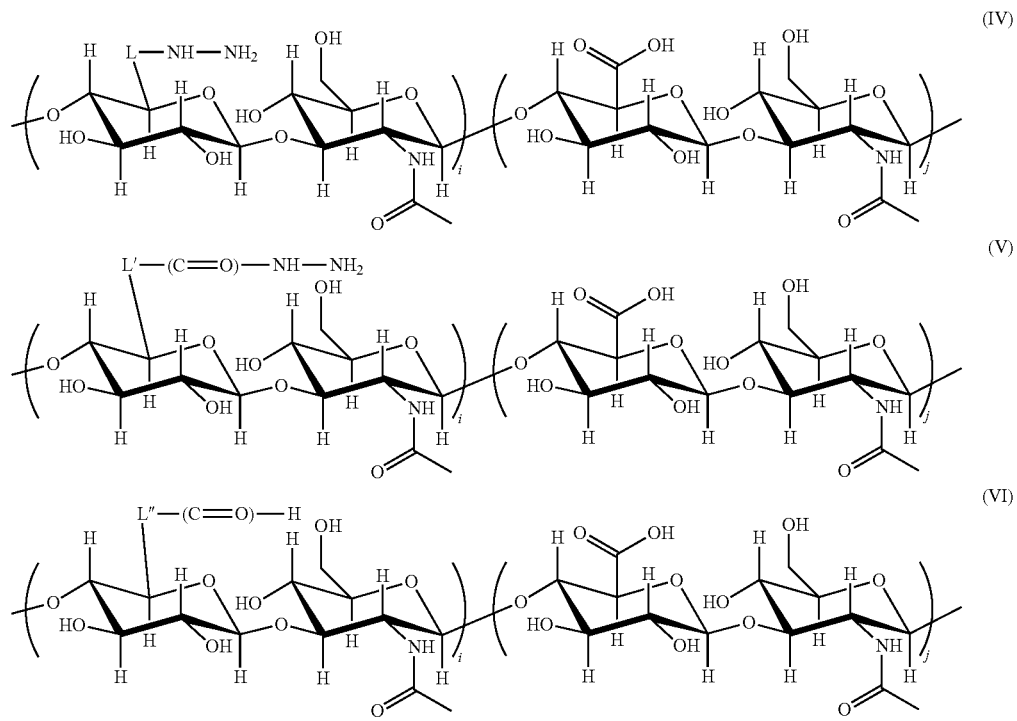

In chemical structures (IV) through (VI), i is an integer greater than or equal to 1, j is an integer greater than or equal to 0, and a sum of i and j is an integer greater than or equal to 1, such as i+j≥2, ≥5, ≥10, ≥15, ≥20, ≥50, ≥100, or ≥200.

Hydrogel compositions of some embodiments of this disclosure can be formed by mixing or otherwise combining aqueous solutions of at least two different modified water-soluble polymers, a first one of which is a hydrazine or hydrazide-modified polymer, such as given by chemical structure (I) or (II) (or (Ia) or (IIa)), and a second one of which is an aldehyde-modified polymer, such as given by chemical structure (III) (or (IIIa)). Mixing induces crosslinking of the polymers through the formation of hydrazone bonds, yielding a crosslinked polymer network dispersed in water, and where the hydrazone bonds can be represented as:

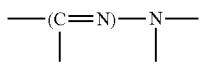

$$-(C=N)-N- \qquad (VII)$$

Mixing of the polymers can be performed in conjunction or sequentially with at least one biocompatible, small molecule catalyst, such as one having a molecular weight of no greater than about 1 kDa, no greater than about 900 Da, or no greater than about 500 Da. Examples of catalysts include those including acidic functional groups, basic functional groups, or both. For example, suitable catalysts can include heterocyclic aromatic compounds, such as aminoalkyl-substituted N-heterocyclic aromatic compounds like 2-(aminomethyl)benzimidazole and its sulfonated or other derivatives. As another example, suitable catalysts can include aromatic acid compounds such as anthranilic acid and its derivatives like 2-aminobenzenephosphonic acid. As another example, suitable catalysts can include aromatic alcohol compounds, such as 2-aminophenols and its derivatives. Suitable catalysts can be cationic, anionic, or zwitterionic under physiological conditions (e.g., pH of about 7.4). Suitable catalysts can have a $pK_a$ (logarithm of its acid dissociation constant) in a range of about 6 to about 9, about 6 to about 8.5, about 6 to about 8, about 6.5 to about 8, or about 7 to about 8. Mixing of the polymers can be performed in conjunction or sequentially with cells or bioactive therapeutics.

In some embodiments, a polymer content of a hydrogel composition can be in a range from about 0.1 wt. % to about 30 wt. %, about 0.5 wt. % to about 30 wt. %, about 0.5 wt. % to about 25 wt. %, about 0.5 wt. % to about 20 wt. %, about 0.5 wt. % to about 15 wt. %, or about 1 wt. % to about 10 wt. %, with a remaining content including water as a liquid medium, one or more catalysts, and cells or bioactive therapeutics.

In some embodiments, a catalyst concentration or loading of a hydrogel composition can be in a range from about 0.1 millimolar (mM) to about 1 molar (M), about 0.5 mM to about 500 mM, about 0.5 mM to about 400 mM, about 0.5 mM to about 300 mM, about 0.5 mM to about 200 mM, about 0.5 mM to about 100 mM, about 1 mM to about 100 mM, about 1 mM to about 5 mM, or about 5 mM to about 100 mM.

EXAMPLE

The following example describes specific aspects of some embodiments of this disclosure to illustrate and provide a description for those of ordinary skill in the art. The example should not be construed as limiting this disclosure, as the example merely provides specific methodology useful in understanding and practicing some embodiments of this disclosure.

Figure 2:
FIG. 2. Chemical structures of hydrazine and aldehyde modified HA polymers (left) and catalysts used to accelerate hydrazone exchange (right).

Temporally Modulating Exchange Kinetics of Dynamic Hyaluronan Hydrogels by a Biocompatible Organocatalyst to Achieve Both High Injectability and High Stability Hyaluronic acid (HA) is chosen as a polymer backbone to form hydrogels, since it is a biocompatible, naturally abundant polysaccharide in human tissue and plays an important role in many biological processes. HA is a relatively sensitive natural polymer that can degrade under acidic, basic, and oxidative conditions. Therefore, a mild strategy is developed to modify HA with hydrazine and aldehyde groups without backbone degradation (FIG. 6): a pre-determined amount of alkyne functionalities were attached to HA via carbodiimide coupling, which were then functionalized with hydrazine and aldehyde groups via copper catalyzed "click" reaction (FIG. 2).

HA-hydrazone hydrogels can be formed by mixing dilute solutions of hydrazine-modified HA and aldehyde-modified HA in phosphate buffered saline (PBS, pH of about 7.4) at about 37° C. HA with about 60 kDa molecular weight is selected, and about 127% of its carboxylate groups are modified with aldehyde or hydrazine (FIG. 2) to evaluate the effect of incorporated catalyst on the properties of formed hydrogels and their efficacy for cyto-protection during injection. These HA hydrogels exhibited stress-relaxation behavior as a result of the dynamic exchange of the hydrazone crosslinking. And their mechanical properties can be tuned using several parameters, such as HA concentration, chemical structure of hydrazone, molecular weight (MW) of HA, and degree of modification on HA.

Figure 3:
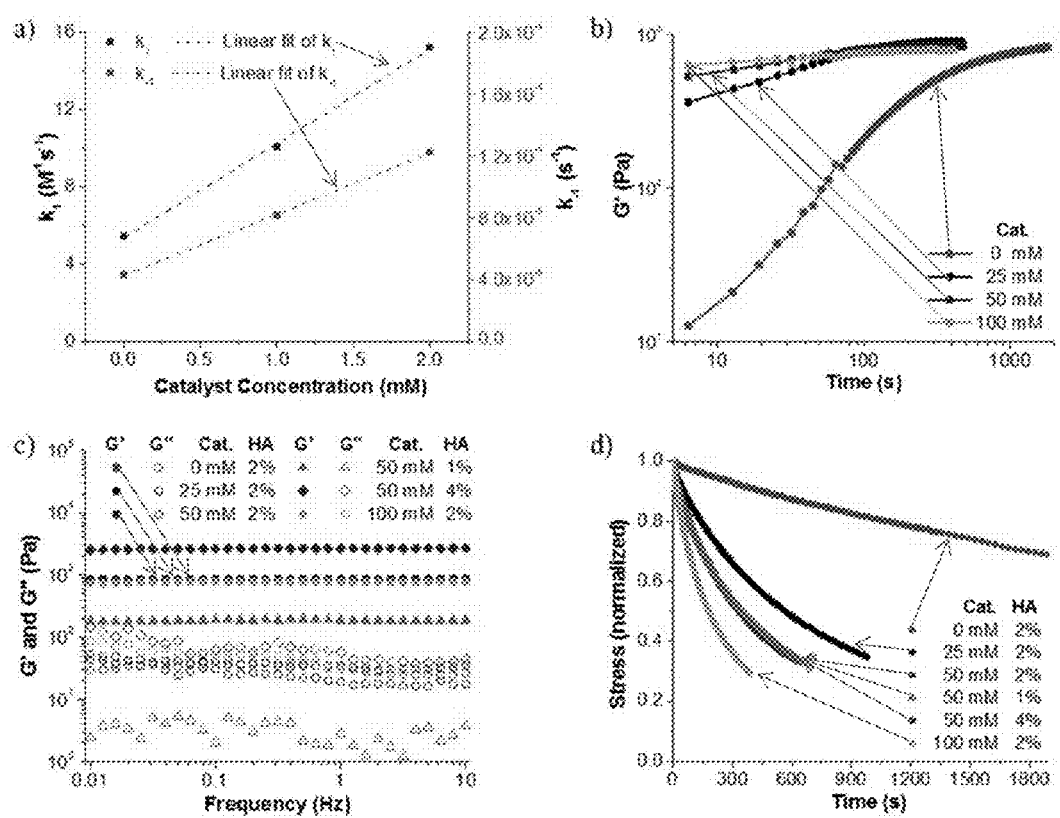
FIG. 3. Effects of catalyst 1 on the hydrazone exchange reaction and properties of hydrazone-crosslinked HA hydrogels. a) Measured first-order dependence of the rates of hydrazone formation ($k_1$) and cleavage ($k_{-1}$) on catalyst concentration. b) Oscillatory time sweep (2 wt. % HA gel) showing the rate of gelation accelerated with increasing the catalyst concentration but the equilibrium modulus of the hydrogels remained substantially the same. c) Oscillatory frequency sweep showing hydrogel modulus independent of the incorporated catalyst concentration but dependent on the HA concentration. d) Stress relaxation accelerated with increasing the catalyst concentration but independent of the HA concentration.

2-(aminomethyl)benzimidazole (1 in FIG. 2) is an efficient catalyst to accelerate hydrazone formation owing to facilitated intramolecular proton transfer in the transition state. The rates for hydrazone formation ($k_1$) and cleavage ($k_{-1}$) in the presence of 1 were measured using model reactions between hydrazine and aldehyde and modeled for a reversible second-order reaction (FIG. 8), and the equilibrium constant ($K_{eq}$) was calculated from these rate constants. 1 exhibited high catalytic activity and first-order dependence on the reaction rate (FIG. 3a). Both $k_1$ and $k_{-1}$ showed about 24, about 47, and about 94-fold enhancement in the presence of about 25, about 50, and about 100 mM of 1, respectively (Table 1), and $K_{eq}$ remained substantially constant and independent of the catalyst concentration. The gelation time of the HA-hydrazone hydrogels was dramatically shortened in the presence of 1. For an about 2 wt. % HA hydrogel, equilibrium gelation was reached in about 30 min without 1 (FIG. 3b). In the presence of about 25 mM of 1, gelation occurred in less than about 60 s and reached a final plateau shear modulus of about 800 Pa in about 5 min (FIG. 3b). Increasing the catalyst loading to about 100 mM further shortened the time to reach equilibrium to about 3 min (FIG. 3b). As shown in the frequency sweep experiment (FIG. 3c), stable gels were formed with a plateau storage modulus (G') of about 1 kPa, which is more than an order of magnitude higher than the loss modulus (G"). The hydrogel plateau modulus remained substantially the same regardless of the catalyst loading (examples shown using about 2 wt. % HA gels at 0, about 25, about 50, and about 100 mM catalyst loadings in FIG. 3c), confirming that the catalyst did not affect the equilibrium network structure or hydrogel modulus. In contrast, altering the HA polymer composition from about 1 to about 4 wt. % increased the plateau modulus (FIG. 3c). The dynamic exchange of hydrazone crosslinks allowed the HA hydrogels to exhibit stress-relaxation behavior (FIG. 3d), which correlates to the ease of flowing under applied force. The rate of stress relaxation under constant strain was quantified by the time for the initially measured stress to relax to half of its original value, $\tau_{1/2}$. The catalyst remarkably enhanced the rate of stress-relaxation for these hydrogels, decreasing $\tau_{1/2}$ from about 75 min without 1 to about 10 min and about 3 min with about 25 mM and about 100 mM of 1, respectively (FIG. 3d). Accelerated hydrazone exchange by an incorporated catalyst also allowed these hydrogels to be readily remolded macroscopically (FIG. 9), facilitating their injection and re-processing. Furthermore, altering the hydrogel stiffness by tuning the HA concentration did not impact the stress-relaxation rate, as shown by the same stress-relaxation profiles between about 1, about 2, and about 4 wt. % HA hydrogels in FIG. 3d. Therefore, the design provides a strategy to tune the modulus and rate of stress relaxation, two important mechanical properties for dynamic hydrogel materials, independently and continuously by polymer concentration and catalyst concentration, respectively.

Figure 4:
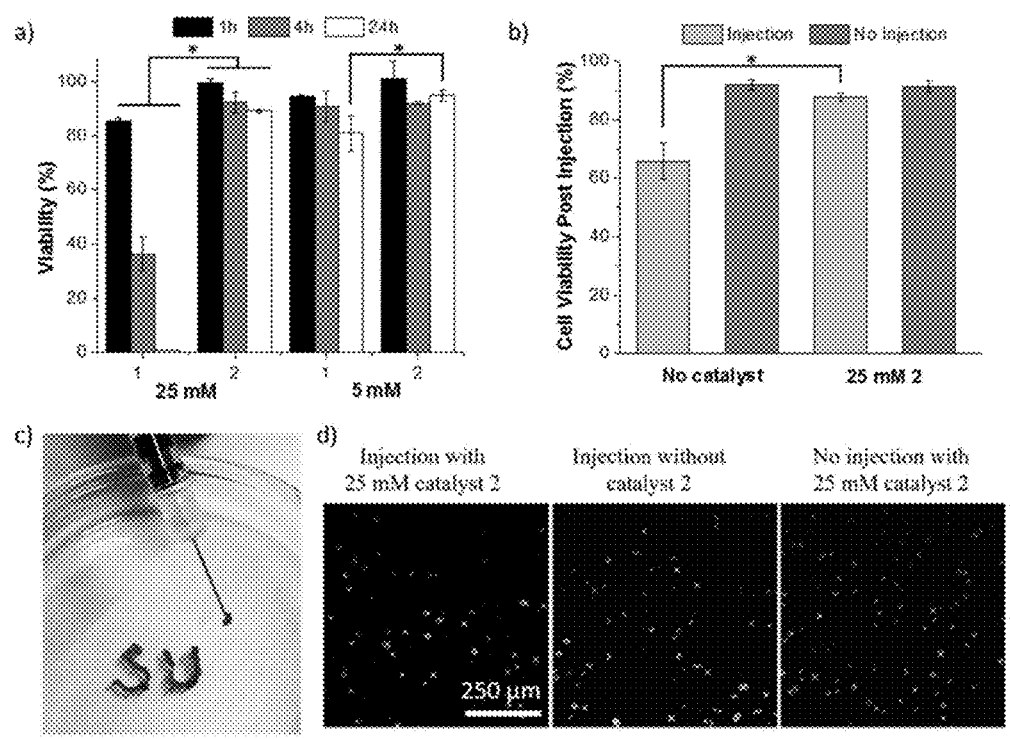
FIG. 4. a) Human Umbilical Vein Endothelial Cell (HUVEC) viability after about 1 h, about 4 h, and about 24 h in culture medium containing about 25 and about 5 mM catalysts 1 and 2 (*p<0.05, n≥3). b) Cell viability without or with about 25 mM catalyst 2 following in vitro injection of about 2 wt. % hydrogel into a Petri dish through a 28-G syringe needle at about 0.05 mL min$^{-1}$ (*p<0.05, n≥3). c) Image of ejecting gels through a 28-G needle without clogging (Phenol red was added to color the hydrogel for visualization). d) Images of LIVE/DEAD analysis for gel-encapsulated HUVECs showing viability after injection in the presence and absence of catalyst 2 and with no injection in the presence of catalyst 2.
Figure 10:
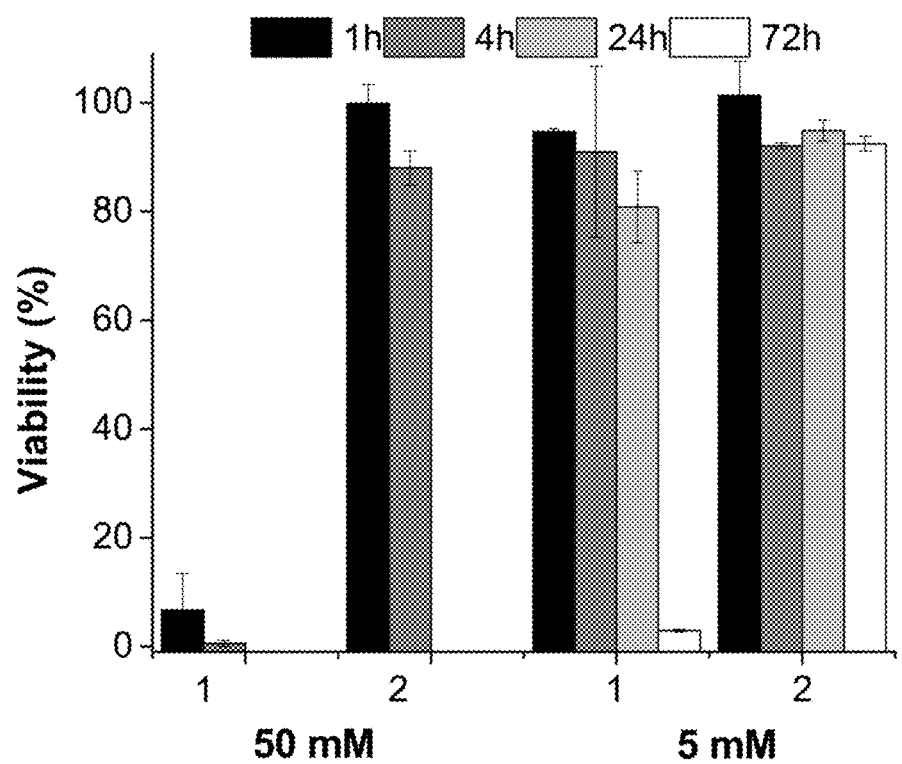
FIG. 10. HUVEC viability at about 1 h and about 4 h after exposure to culture medium containing about 50 mM catalyst 1 and 2, and at about 1 h, about 4 h, about 24 h and about 72 h after exposure to culture medium containing about 5 mM catalyst 1 and 2.
Figure 11:
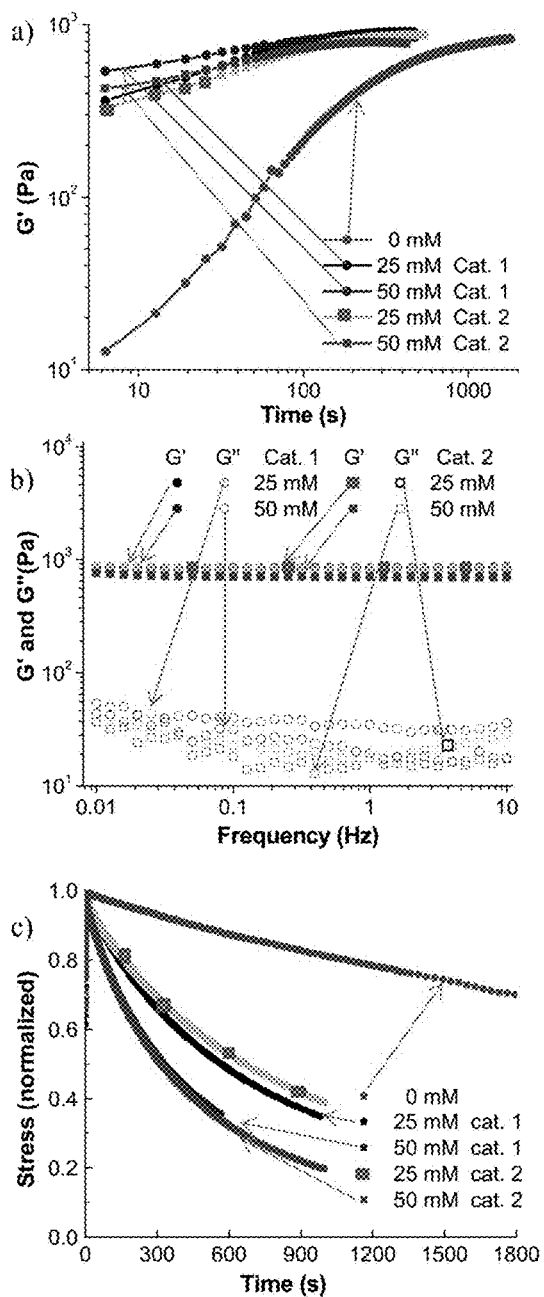
FIG. 11. Nearly identical catalytic efficiency of 2 as compared to 1, as shown by nearly identically accelerated gelation time and tunable stress-relaxation rates in the presence of 1 or 2 at the same concentration. a) Oscillatory time sweep (2 wt. % gel) showing the rate of gelation and final storage modulus of the hydrogels in the presence of 1 or 2. b) Oscillatory frequency sweep showing nearly identical modulus in the presence of 1 or 2. c) Stress relaxation showing similar relaxation rates in the presence of 1 or 2.

High cyto-compatibility is desired for catalysts used in this design for biomedical applications. In view of the cationic nature of catalyst 1, a sulfonated derivative of 1 is synthesized, thus converting it to a zwitterionic form, 2, to impart enhanced biocompatibility. Cyto-compatibility of both 1 and 2 were evaluated using two-dimensional (2D) cultures of Human Umbilical Vein Endothelial Cells (HUVECs). HUVECs were chosen as an example test cell line because they are a clinically relevant human cell type that has been broadly explored for tissue engineering and regenerative medicine applications. Significant cell death was observed in the presence of about 25 mM of 1 within several hours (FIG. 4a). In sharp contrast, 2 exhibited high cyto-compatibility, with about 85% cells remaining viable after about 24 h exposure at about 25 mM and negligible cell death at about 5 mM even after about 3 days (FIG. 4a and FIG. 10). Such dramatically improved cyto-compatibility of 2 was attributed to its zwitterionic nature. Of note, 2 was found to exhibit similar catalytic efficiency to 1, and yielded almost identically accelerated gelation time and tunable stress-relaxation rates as 1 at the same catalyst concentration (FIG. 11).

Evaluation was performed on the effect of catalyst 2 incorporated in HA-hydrazone hydrogels on the protection of encapsulated cells during injection. HUVECs were homogeneously encapsulated in about 2 wt. % hydrogels containing about 25 mM of 2 by rapidly mixing the cells suspended in HA solutions with catalyst and transferring to a syringe. Hydrogel was rapidly formed in the syringe and ejected through a 28-gauge syringe needle. A syringe pump was used for all cell injection experiments to ensure consistent flow rate for accurate comparison between all samples. In the presence of about 25 mM of 2, the hydrogels can be readily ejected through the thin needle without clogging (FIG. 4c). In contrast, in the absence of a catalyst, the same hydrogel experienced high resistance to flow.

After injection, cells encapsulated in the hydrogels were incubated for about 20 min, and cell viability was then analyzed using a LIVE/DEAD staining assay. In the control gel without catalyst 2, the injection led to significant cell death with about 65% viability, presumably due to membrane damage during injection (FIG. 4b,d). In contrast, the presence of about 25 mM of 2 significantly increased the cell viability to about 87% after injection, which is similar to the viability of cells encapsulated in identically prepared hydrogels without injection (FIG. 4b,d). This result strongly indicated that the enhanced network dynamics of hydrogels in the presence of the catalyst improved injectability and provided better protection for encapsulated cells during flow.

Figure 5:
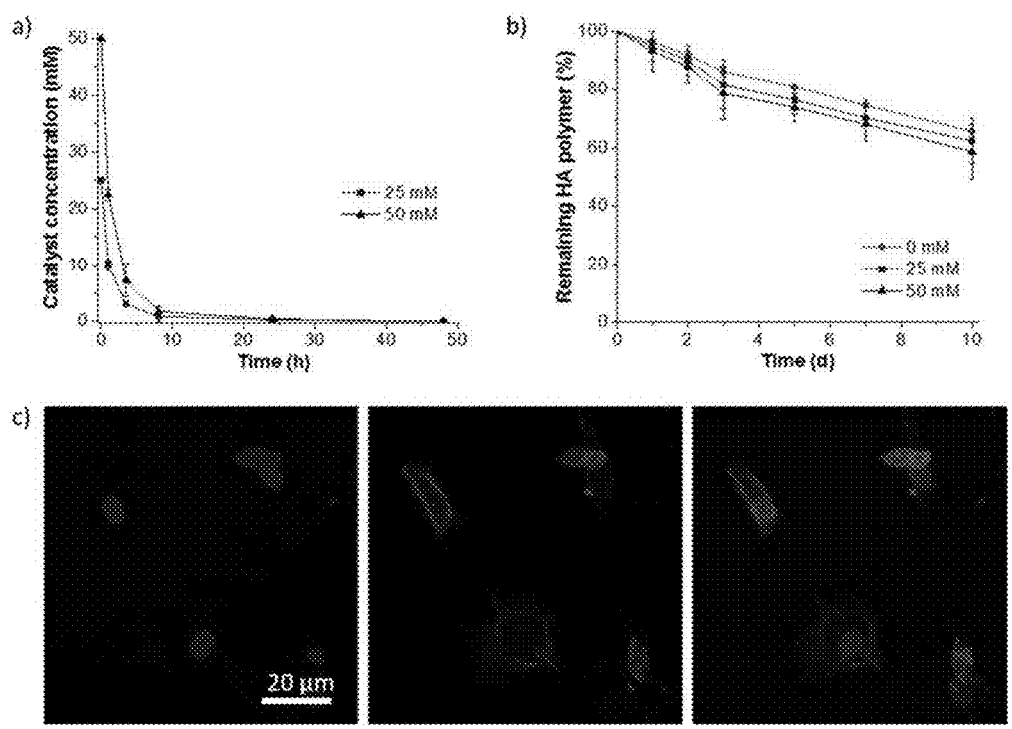
FIG. 5. a) Concentration of remaining catalyst 2 inside hydrogels over time after immersion of catalyst-containing hydrogels in phosphate buffered saline (PBS), showing rapid diffusion out of the hydrogels. b) Erosion kinetics of hydrogels with and without catalyst 2 at about 37° C. over about 10 days. c) Cell spreading in hydrogels at about 72 h post-injection with initially about 25 mM of 2 during injection (Left panel: blue DAPI nuclear staining; middle panel: red actin cytoskeleton staining; right panel: merged image).
Figure 12:
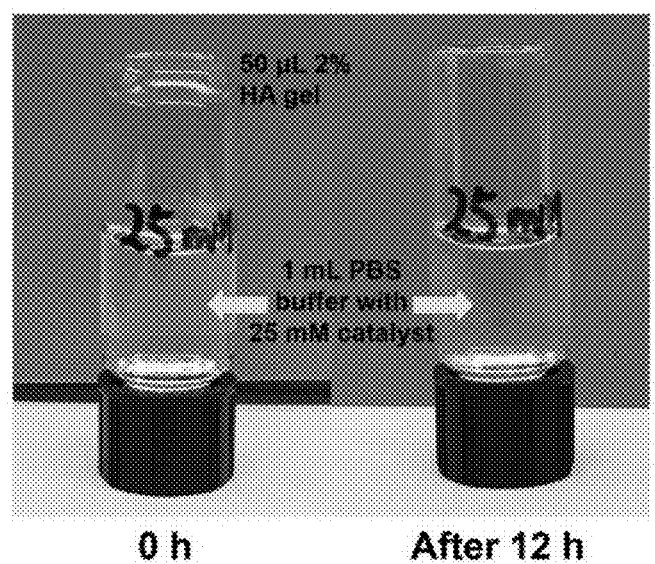
FIG. 12. Hydrogel containing about 25 mM catalyst substantially completely dissolved within about 12 h when the catalyst diffusion out of the gel was prevented by immersing in PBS buffer containing about 25 mM catalyst.

Long-term stability of hydrogel scaffolds is often desired to provide support for cell adhesion and growth after cell injection. Rapid hydrogel erosion is a challenge for many dynamic and injectable hydrogels. It is proposed that rapid passive diffusion of the dissolved small molecule catalyst away from the hydrogel post-injection would slow down the dynamic exchange of hydrazone crosslinks and thus enhance the hydrogel stability. Therefore evaluation was performed to monitor the diffusion of 2, which was incorporated in the hydrogel at either about 25 mM or about 50 mM initial concentration, into the buffer solution after injection by monitoring its absorption at about 281 nm. After about 50 μL hydrogel was injected and immersed in about 1 mL PBS, about 60% of 2 diffused out of the hydrogel within about 1 h, and less than about 1% remained inside the gel after about 8 h (FIG. 5a). To examine whether the rapid diffusion and thus removal of catalyst can increase the long-term stability of the hydrogels, comparison is performed of the erosion rate of hydrogels with different initial concentrations of incorporated catalyst. Hydrogels without incorporated catalyst exhibited an initial erosion rate of about 3.5% per day (over about 10 days), as determined by fitting the erosion data to a zero-order kinetic model, and about 65% of the hydrogel mass was retained after about 10 days. Hydrogels initially containing about 25 mM or about 50 mM of catalyst 2 had erosion rates of about 3.8 and about 4.1% per day respectively, similar to those without a catalyst (FIG. 5b), presumably due to rapid diffusion of 2 out of the hydrogels. In contrast, when diffusion of 2 away from the hydrogel was prevented by immersing the hydrogel into a buffer solution containing about 25 mM of 2, the hydrogel was completely dissolved within about 12 h (FIG. 12). Therefore, the strategy temporally modulates the exchange rate of dynamic crosslinking, achieving the desired short-term injectability and long-term stability at different stages of the application from the same hydrogel network.

To test the ability of the HA hydrogels to support cellular growth as a scaffold after injection, cell-adhesive Arg-Gly-Asp (RGD) peptide motifs are attached to the hydrazine-functionalized HA polymer. HUVECs were encapsulated within the RGD-presenting HA-hydrazone hydrogels in the presence of about 25 mM of 2, injected through a 28-gauge needle into a Petri dish, and cultured under physiological conditions in EBM-2 (Endothelial Growth Basal Medium) for about 3 days. Cell morphology was analyzed by staining and imaging of the cell nuclei and actin cytoskeleton. HUVECs encapsulated within the hydrogels demonstrated a spread morphology (FIG. 5c).

In summary, this example sets forth a strategy to temporally modulate the exchange kinetics of dynamically cross-linked hydrogels using a biocompatible organic catalyst to provide high injectability and high stability at different stages of cell delivery. In this strategy, the cyto-compatible sulfonated amino-benzimidazole functions as an effective catalyst to temporally accelerate the rates of formation and exchange of dynamic covalent hydrazone crosslinks in HA-based hydrogels. As a result, the presence of the catalyst enhances the rates of gelation and stress-relaxation, but does not alter the hydrogel network structure nor its storage modulus, which allowed independent and continuous tuning of the stiffness and stress-relaxation rate of the hydrogels by varying the polymer concentration and catalyst loading, respectively. The accelerated exchange of crosslinking led to enhanced injectability of the hydrogels and improved cell protection during injection. As the catalyst rapidly diffused out of the hydrogels after injection, the hydrogels gained high stability and slow erosion post-injection to provide a long-term, cell-adhesive scaffold for cell culture. This effective design bestows hydrogels with both high injectability and stability, two often conflicting but desired properties of dynamic hydrogels used for biomedical applications. Considering the broad applications of biocompatible hydrazone chemistry, this strategy can be applicable to a wide range of dynamic hydrogel materials for therapeutic cell delivery and 3D printing of encapsulated cell scaffolds.

Experimental Section

Materials. Sodium hyaluronate (about 60 kDa) was purchased from Lifecore. All other chemicals were obtained from commercial sources and used as received unless otherwise noted. 2-(2-(2-(azidoethoxy)ethoxy)ethoxy)acetaldehyde (S1) was prepared according to reported procedures. Analytical thin-layer chromatography (TLC) was carried out using about 0.2 mm silica gel plates (silica gel 60, F254, EMD chemical).

Characterizations. $^1$H and $^{13}$C NMR spectra were recorded using 400 Varian NMR spectrometers. Chemical shifts are reported in ppm using the residual protiated solvent as an internal standard (CDCl$_3$ $^1$H: about 7.26 ppm and $^{13}$C: about 77.0 ppm; D$_2$O $^1$H: about 4.79 ppm; DMSO-d6 $^1$H: about 2.50 ppm and $^{13}$C: about 39.5 ppm). High-performance liquid chromatography-mass spectrometry (HPLC-MS) was performed in acetonitrile/water containing about 0.1% formic acid on an Alliance e2695 Separations Module using an)(Bridge 10 μm C18 column in series with a 2489 UV/Visible Detector and an Acquity QDa Detector (all from Waters Corporation). Rheological characterization was performed using an AR-G2 controlled stress rheometer at about 37° C. All measurements were performed using an about 20 mm cone plate geometry and analyzed using TRIOS Software. UV-Vis spectra were recorded on a SpectraMax M2 Spectrophotometer. Aqueous size exclusion chromatography (SEC) was carried out using Shimadzu LC-20AD high performance liquid chromatography with a refractive index detector.

1. Synthetic Procedures

N-(3-azidopropyl)-2-hydrazineylacetamide (S2)

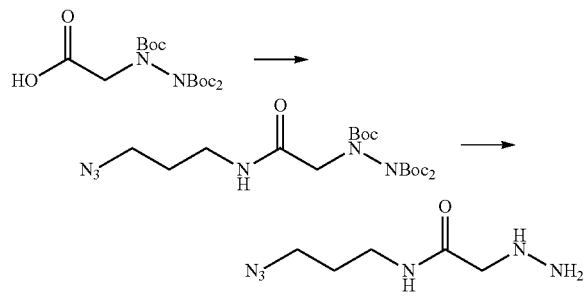

N-(3-azidopropyl)-2-hydrazineylacetamide was synthesized according to reported procedures with modification. Tri-Boc-hydrazinoacetic acid (about 2.5 g, about 6.4 mmol, about 1 eq.), azidopropyl amine (about 0.84 g, about 8.3 mmol, about 1.3 eq.), 1-ethyl-3-(3-dimethylaminopropyl) carbodiimide (about 1.6 g, about 8.3 mmol, about 1.3 eq.), and 4-dimethylaminopyridine (about 0.16 g, about 1.3 mmol, about 0.2 eq.) were dissolved in about 20 mL methylene chloride (DCM). The solution was stirred at room temperature overnight. The solvent was removed under reduced pressure, and the residue was purified by silica gel chromatography (ethyl acetate/hexane, about 1:1 v/v) to obtain the Boc-protected product as a colorless oil (about 2.8 g, about 92% yield). The isolated Boc-protected product was then dissolved in about 10 mL of about 4 M HCl in dioxane. After stirring at room temperature for about 4 h, the product precipitated from the solution as a sticky yellow solid (about 1.2 g, about 95% yield). $^1$H NMR (400 MHz, D$_2$O) δ 3.71 (s, 2H), 3.33 (t, J=6.7 Hz, 2H), 3.26 (t, J=6.7 Hz, 2H) 1.74 (dd, J=6.7 Hz, 2H). $^{13}$C NMR (100 MHz, D$_2$O) δ 169.57, 50.65, 48.72, 36.70, 27.64. MS (ESI) m/z [M$^-$H$^+$]: 173.05.

Catalyst 2

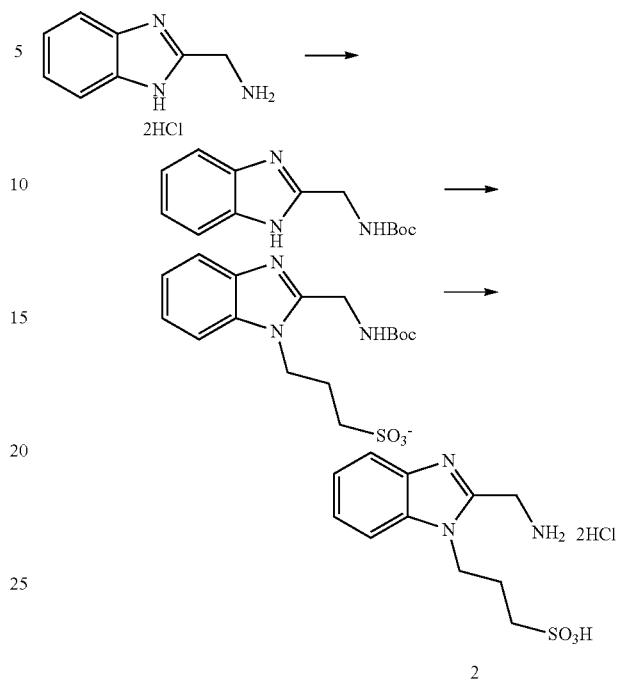

2-(Aminomethyl)benzimidazole dihydrochloride (about 600 mg, about 2.7 mmol, about 1 eq.) and trimethylamine (about 2.3 mL, about 16.4 mmol, about 6 eq.) were dissolved in about 12 mL tetrahydrofuran (THF). Di-tert-butyl dicarbonate (about 595 mg, about 2.7 mmol, about 1 eq.), dissolved in about 3 mL THF, was then added dropwise to the mixture at 0° C. The solution was allowed to warm up to room temperature and stirred at room temperature overnight. The mixture was then filtered and the filtrated was concentrated. The crude product was purified by silica gel chromatography (DCM/methanol, about 93:7 v/v) to obtain the Boc-protected product as white solid (about 550 mg, about 82% yield). This Boc-protected benzimidazole (about 200 mg, about 0.81 mmol, about 1 eq.), 1,3-propane sultone (about 109 mg, about 0.89 mmol, about 1.1 eq.), and potassium hydroxide (about 50 mg, about 0.89 mmol, about 1.1 eq.) were dissolved in about 3 mL dimethylformamide (DMF). The solution was stirred at about 60° C. for about 2d. The solvent was removed under reduced pressure and the residue was purified by silica gel chromatography (DCM/methanol, about 4:1 v/v) to obtain the product as white solid (about 160 mg, about 54% yield). $^1$H NMR (400 MHz, DMSO-d6) δ 7.67 (d, J=7.9 Hz, 1H), 7.59 (d, J=7.7 Hz, 1H), 7.52 (t, J=5.9 Hz, 1H), 7.25 (m, 2H), 4.47 (d, J=5.9 Hz, 2H), 4.40 (t, J=7.6 Hz, 2H), 2.46 (t, J=6.9 Hz, 2H), 2.01 (m, 2H), 1.38 (s, 9H). $^{13}$C NMR (100 MHz, DMSO-d6) δ 163.74, 156.28, 152.53, 135.41, 123.38, 122.96, 118.56, 111.55, 79.14, 48.72, 43.00, 37.58, 28.86, 26.43. MS (ESI) m/z [M$^-$H$^+$]: 370.2.

The isolated Boc-protected product was then dissolved in about 3 mL of about 4 M HCl in dioxane. After stirring at room temperature overnight, the product precipitated from the solution. The solid was then washed with ether 3 times and isopropyl alcohol once to obtain catalyst 2 as yellowish solid (about 140 mg, about 94% yield). $^1$H NMR (400 MHz, DMSO-d6) δ 7.89 (d, J=7.8 Hz, 1H), 7.78 (d, J=8.5 Hz, 1H), 7.52 (m, 2H), 4.58 (m, 4H), 2.54 (t, J=6.7 Hz, 2H), 2.11 (m, 2H). $^{13}$C NMR (100 MHz, DMSO-d6) δ 147.83, 136.12, 134.02, 125.39, 125.30, 117.23, 112.92, 48.05, 43.71, 34.44, 26.02. MS (ESI) m/z [M⁻H⁺]: 270.1

Hyaluronic Acid (HA) Modification

HA Modification with Alkyne

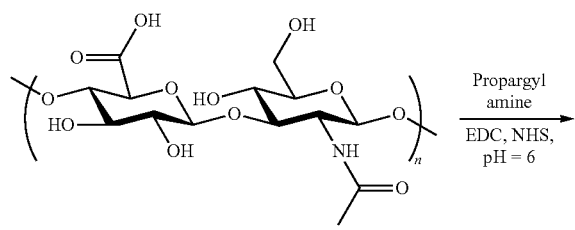

Sodium hyaluronate was dissolved in 2-(N-Morpholino) ethanesulfonic acid (MES) buffer (about 0.2 M, pH of about 4.5) to a concentration of about 10 mg/mL. To this solution, N-hydroxysuccinimide (about 223 mg per gram of HA, about 0.8 eq. to the HA dimer unit), 1-ethyl-3-(3-dimethyl-aminopropyl) carbodiimide (about 372 mg per gram HA, about 0.8 eq.) and propargyl amine (about 128 µL per gram HA, about 0.8 eq.) were added successively. After adjusting pH to about 6, the mixture was stirred at room temperature for about 4 h. The solution was then dialyzed against de-ionized (DI) water for about 3 d and lyophilized to give a white powder. The degree of modification was quantified by ¹H NMR spectroscopy after "click" functionalization.

HA Modification with Hydrazine and Aldehyde

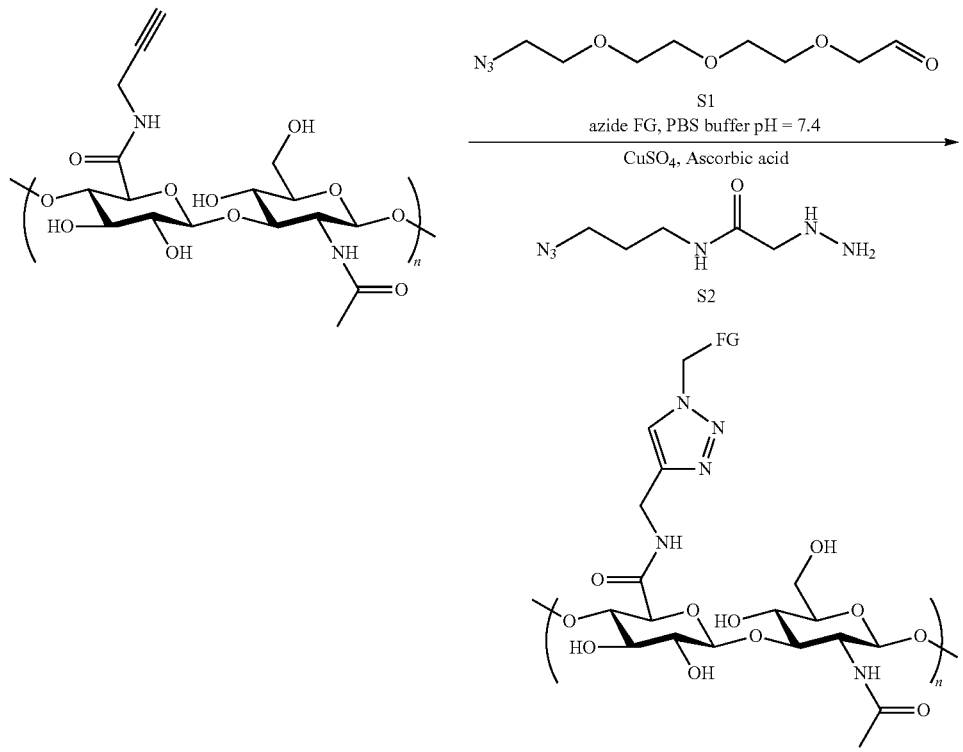

-continued

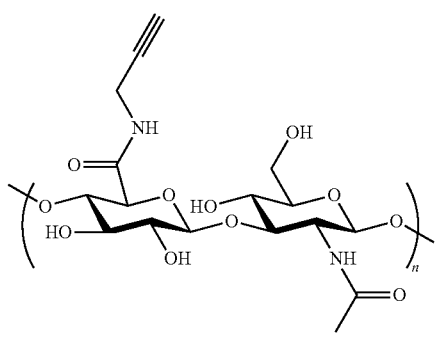

Figure 6:
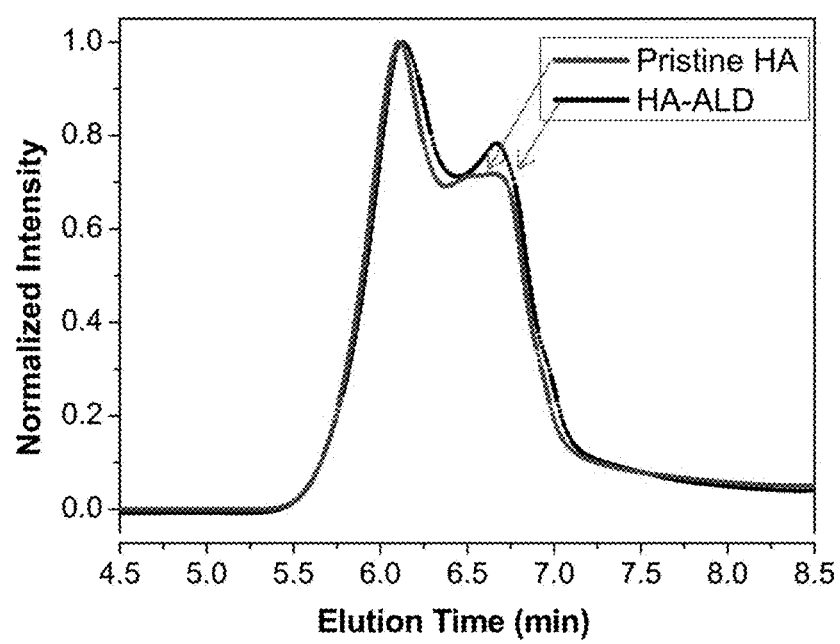
FIG. 6. Size exclusion chromatography (SEC) traces of pristine HA and aldehyde-modified HA (HA-ALD). No change in molecular weight distribution or degradation of HA was observed after modification, indicating that the mild modification procedure is compatible with HA.
Figure 7:
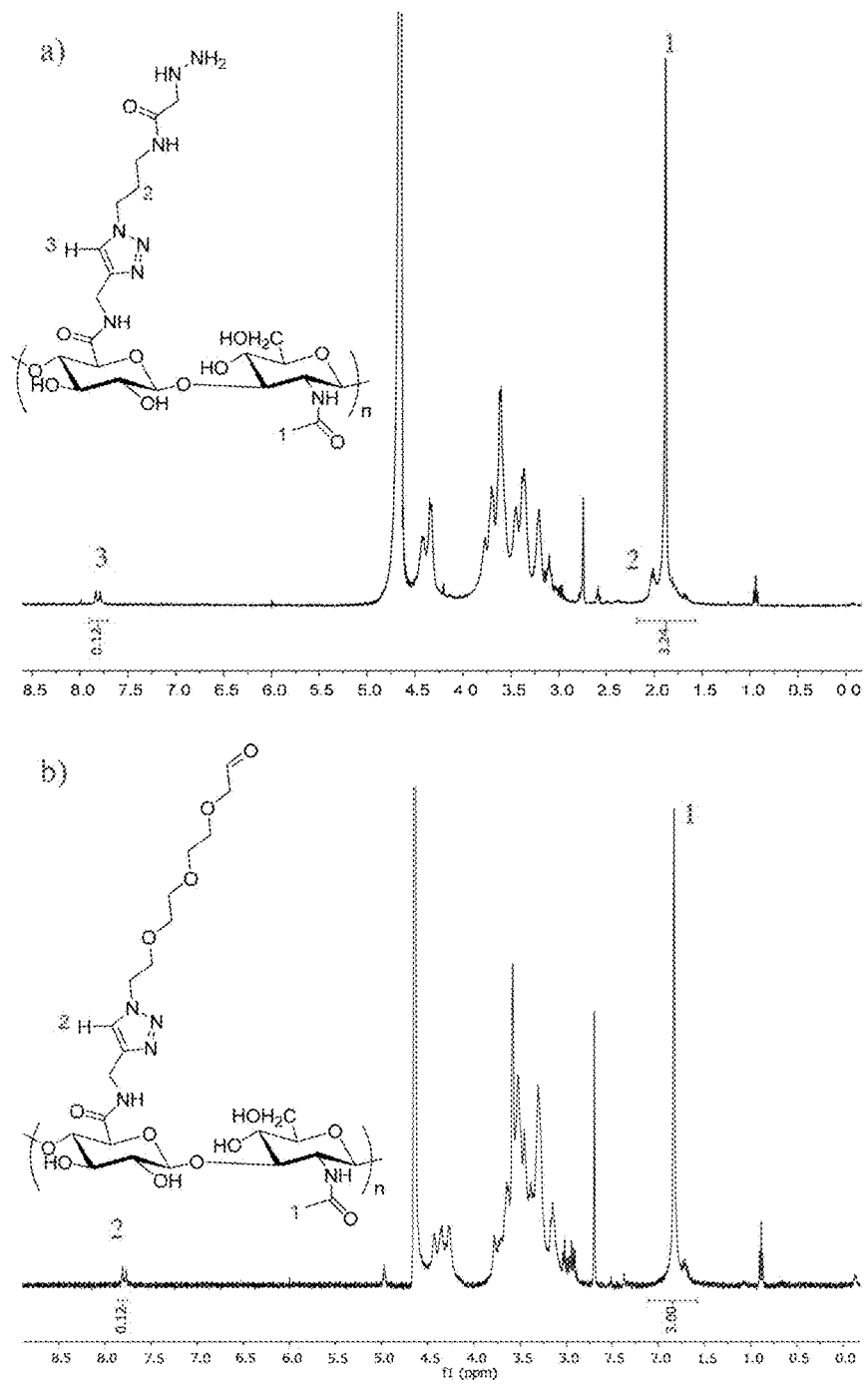
FIG. 7. $^1$H NMR spectrum ($D_2O$) of a) HA modified with hydrazine (HA-HYN) and b) HA modified with aldehyde (HA-ALD).

HA-alkyne (about 300 mg) was dissolved in PBS (pH of about 7.4) at 2 wt. % followed by the addition of azido-aldehyde (S1) or azido-hydrazine (S2) (about 100 mg, about 1 eq. to HA dimer unit). The solution was then bubbled with $N_2$ for about 30 min. Copper (II) sulfate pentahydrate (about 0.76 mg, about 0.004 eq. to HA dimer unit) and sodium ascorbate (about 8.7 mg, about 0.06 eq. to HA dimer unit) were dissolved in DI water, bubbled with $N_2$, and added to HA solution. After stirring at room temperature for about 1 d, the mixture was dialyzed against DI water for about 3 d and lyophilized. The degree of modification on HA was quantified using ¹H NMR spectroscopy by integration of the proton signal on triazole group ($\delta$=7.85, 1H) relative to that of the methyl groups on N-acetylglucosamine of HA backbone ($\delta$=1.8, 3H). ¹H NMR integration indicated that about 12% of the carboxylate groups on the HA backbone have been functionalized (FIGS. 6-7).

HA Modification with RGD

RGD-HA was prepared by coupling the oligopeptide GGGGRGDSP (Peptides International) to HA using carbodiimide chemistry. Sodium hyaluronate (about 250 mg) was dissolved in MES buffer (about 0.1 M, pH of about 6.5) to a concentration of about 10 mg/mL. To this solution, N-Hydroxysulfosuccinimide sodium salt (about 51 mg), 1-ethyl-3-(3-dimethylaminopropyl) carbodiimide (about 91 mg) and RGD peptide (about 60 mg) were added successively. The mixture was stirred at room temperature for about 20 h and quenched by the addition of hydroxylamine hydrochloride (about 180 mg). The solution was then dialyzed against DI water for about 3 d and lyophilized to give a white powder. The coupling efficiency using this procedure was characterized by bicinchoninic acid (BCA) assay, which indicated that about 6% of the carboxylate groups on the HA backbone have been functionalized. This corresponds to the density of about 1.5 mM RGD in an about 2 wt. % HA gel. RGD-HA was then modified with hydrazine groups using the same procedure as described in the previous section.

2. Hydrogel Preparation

HA-hydrazine and HA-aldehyde were first solubilized in PBS (1×, pH of about 7.4) at 5 wt. % respectively. Catalyst 1 and 2 were dissolved in PBS (1×, pH of about 7.4) and adjusted pH to about 7.4 at a stock concentration of about 250 mM. HA hydrogels were prepared by mixing HA-hydrazine, catalyst, and HA-aldehyde stock solutions successively at hydrazine to aldehyde (molar) ratio of about 1:1. The volumes of stock solutions were adjusted to make gels with different formulations.

3. Rheological Tests

Rheological characterization was performed on a stress-controlled rheometer (AR-G2, TA instrument) using a 20 mm cone plate. About 45 µL of a sample was loaded immediately onto the rheometer after mixing to gel in situ on the rheometer and a humidity chamber was secured in place to prevent dehydration. All the tests were performed at about 37° C. Time sweeps were performed at about 1 Hz at about 1% constant strain. Frequency sweeps were performed from about 0.1 to about 10 Hz at about 1% constant strain. Stress relaxation experiments were performed at about 10% strain.

4. Kinetic Measurements on Hydrazone Exchange

Figure 8:
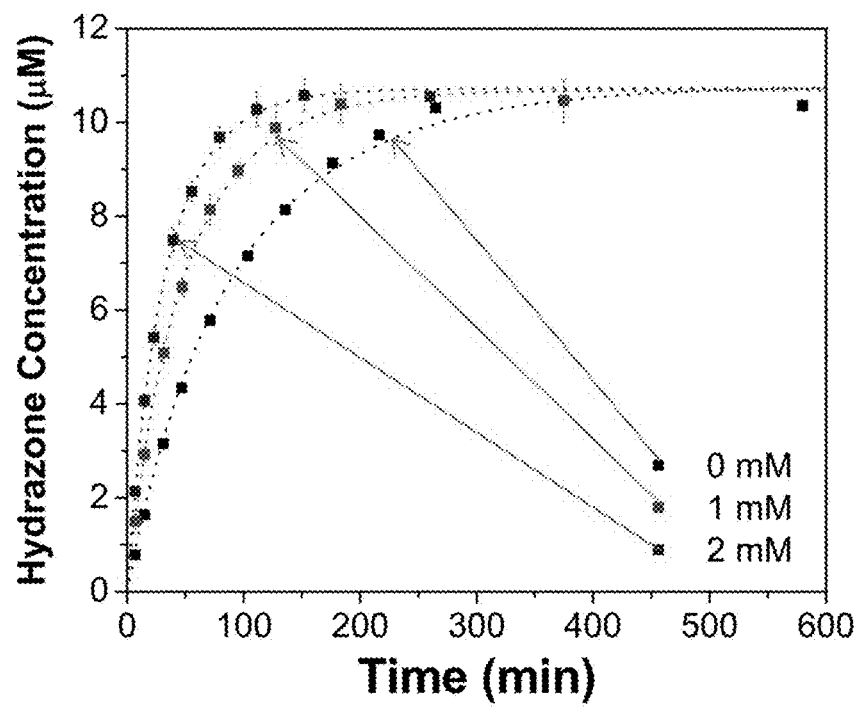
FIG. 8. Formation of hydrazone in model reactions at about 20 µM reactants at about 37° C. in PBS buffer (1×, pH of about 7.4) in the presence of 0 mM, about 1 mM and about 2 mM of catalyst 1. Each data point represents the mean value from three independent kinetics tests. The dashed line represents the fitting of raw data using the $2^{nd}$ order reversible reaction kinetics model.
Figure 9:
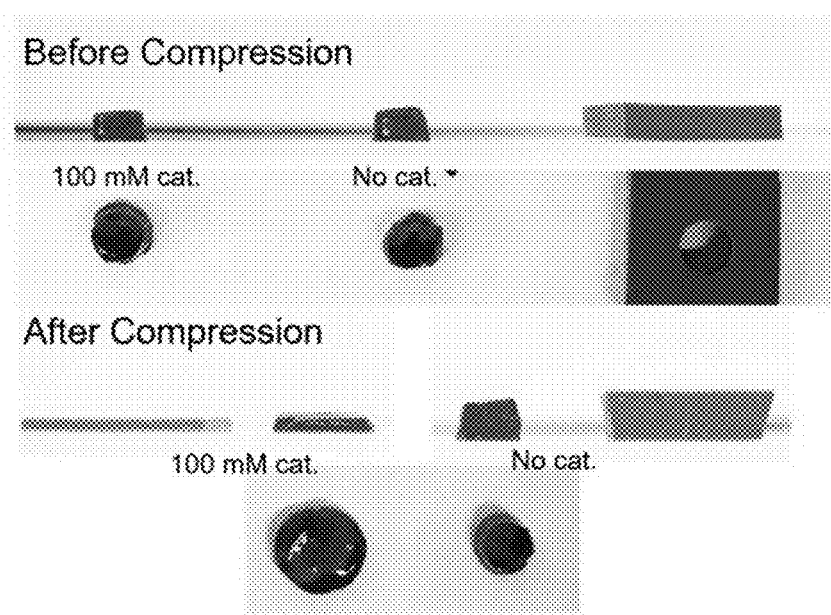
FIG. 9. Compression test showing remoldability of HA-hydrazone hydrogels was improved with the addition of a catalyst. After being pressed into molds from about 2.4 mm to about 0.6 mm in height for about 5 min, a hydrogel containing about 100 mM of 1 adopted the height of the mold while a hydrogel without the catalyst was not remolded (retaining its original shape) within this short time window (about 5 min).

For the reactions performed in the absence of catalyst, about 10 µL of hydrazine and about 10 µL of aldehyde stock solutions were added to about 980 µL PBS buffer (1×, pH of about 7.4). For the reactions performed in the presence of catalyst 1, the appropriate amount of catalyst 1, hydrazine, and aldehyde were sequentially added to PBS buffer (1×, pH of about 7.4) from their stock solutions, maintaining the same concentrations for hydrazine and aldehyde as those without a catalyst. The reactions were performed at about 37° C. in a water bath and followed using HPLC with detection at about 420 nm absorption (HPLC conditions: XBridge 10 µm C18 column; about 40% acetonitrile in PBS buffer (pH of about 7) isocratic elution in about 7 min at a flow rate of about 0.34 mL/min. The concentrations and conversions were calculated from the integrals of the HPLC signals. The kinetic data of hydrazone formation were fitted to a kinetic model for $2^{nd}$ order reactions using Matlab (FIG. 8).

5. Catalyst Diffusion and Hydrogel Erosion Study

HA hydrogels containing 0, about 25, and about 50 mM of catalyst 2 were prepared as described in the previous section. About 50 µL of the hydrogel was prepared in the syringe and ejected through a 28-gauge syringe needle into separate centrifuge tubes for the erosion test. The hydrogel was allowed to cure for about 30 min before immersed in buffer solution. These gels were then immersed in about 1 mL PBS and incubated at about 37° C. All the buffer solutions were collected and replaced by fresh PBS at about 1 h, about 4 h, about 8 h, about 1 d, about 2 d, about 3 d, about 5 d, about 7 d and about 10 d. The remaining hydrogels were degraded by about 2 mg mL$^{-1}$ hyaluronidase to allow determination of remaining hydrogel content for data normalization. Four replicates were prepared in each group. Catalyst diffusion was quantified using UV measurement by monitoring absorption at about 281 nm. HA erosion was quantified by uronic acid assay according to reported procedures.

6. Cell Culture Experiments

Cell Culture

Human Umbilical Vein Endothelial Cells (HUVECs) were obtained from Lonza. HUVECs were expanded in growth medium composed of about 10% fetal bovine serum,

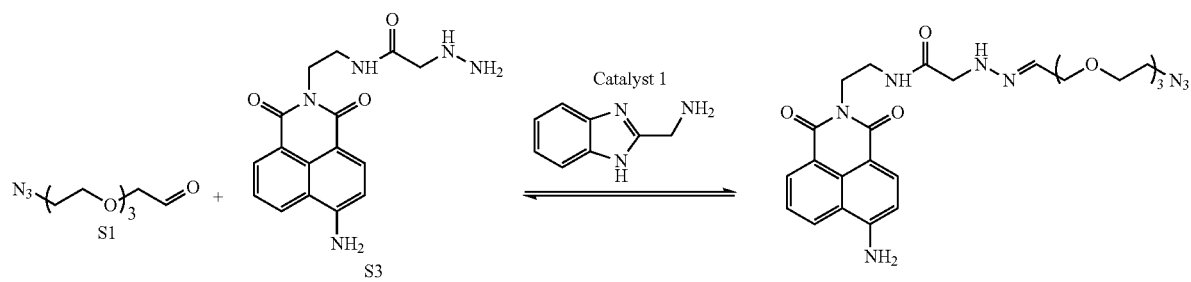

The equilibrium constant ($K_{eq}$) and rate constants for hydrazone formation ($k_1$) and cleavage ($k_{-1}$) between aldehyde S1 and hydrazine S3 as model compounds with different concentrations of catalyst 1 were measured by HPLC. S3 was synthesized by coupling N-(2-aminoethyl)-4-amino-1,8-naphthalimide with hydrazine using carbodiimide chemistry. About 2 mM stock solutions of hydrazine and aldehyde were prepared in a PBS buffer (1×, pH of about 7.4). An about 250 mM stock solution of catalyst 1 was prepared in PBS as described in the previous sections.

about 1% penicillin/streptomycin in EBM-2. The medium was changed every about 3 d and the cells were passaged at about 70% confluency. Cells were used at passage 5 or lower for all experiments.

Catalyst Toxicity

HUVECs pre-seeded in 96-well plates at about $10^4$ cells/well were incubated with catalysts 1 and 2 for about 1 h, about 4 h, about 24 h and about 72 h. Afterwards, the cells were washed with PBS, the cell viability MTT assay was carried out to determine the cell viabilities relative to the control cells incubated with the same volume of PBS.

In Vitro Cell Injection and Quantification of Viability

Cell suspension was first mixed with HA-hydrazine stock solutions before further mixing with catalyst and HA-aldehyde stock solutions. All in vitro injection experiments were performed with about 30 μL gel volume containing about $3 \times 10^4$ cells. For cell injection, the final mixing stage was performed in the barrel of an about 1 mL insulin syringe fitted with a 28 gauge needle. The mixture was allowed to gel for about 15 min before injecting into a circular silicone mold (diameter=about 4 mm, height=about 2.5 mm) within a 24 well plate using a syringe pump (SP220I; World Precision Instruments) at a flow rate of about 0.05 mL min$^{-1}$. Cell viability was determined using LIVE/DEAD viability/cytotoxicity kit (Invitrogen) at about 20 min post-injection and about 3 d post-injection (n=5). Cells were fixed with about 4% paraformaldehyde, permeabilized with about 0.2% Triton X-100 solution in PBS, and stained with rhodamine phalloidin (1:300, Life Technologies) and 4',6-diamidino-2-phenylindole (DAPI, about 1 μg mL$^{-1}$, Life Technologies). Images were collected using a Leica confocal microscope by creating z-stacks of about 200 μm depth with about 2.4 μm intervals between slices in the middle of the hydrogel and then compressing into a maximum projection image. Cell numbers were quantified using ImageJ at each time point.

Statistical Analysis

Certain data in this example are presented as mean±standard deviation. Statistical comparisons were performed by one-way analysis of variance (ANOVA) with Tukey post hoc test. Values were considered to be significantly different when the p value was <0.05.

TABLE 1

Reaction rates and equilibrium constants for hydrazone formation with different concentrations of catalyst 1 calculated from model reaction.

| Conc. of 1 (mM) | $k_1$ (M$^{-1}$s$^{-1}$) | $k_{-1}$ (s$^{-1}$) | $K_{eq}$ (M$^{-1}$) |
|---|---|---|---|
| 0 | 5.44 | $4.29 \times 10^{-5}$ | $1.27 \times 10^5$ |
| 25 | $1.27 \times 10^2$ | $1.03 \times 10^{-3}$ | $1.24 \times 10^5$ |
| 50 | $2.50 \times 10^2$ | $2.03 \times 10^{-3}$ | $1.23 \times 10^5$ |
| 100 | $4.95 \times 10^2$ | $4.01 \times 10^{-3}$ | $1.24 \times 10^5$ |

Conditions: about 137 mM NaCl, about 2.7 mM KCl, about 12 mM phosphate, pH of about 7.4 buffer, about 37° C.

As used herein, the singular terms "a," "an," and "the" may include plural referents unless the context clearly dictates otherwise. Thus, for example, reference to an object may include multiple objects unless the context clearly dictates otherwise.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can encompass a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

As used herein, the term "alkyl" refers to a monovalent, aliphatic hydrocarbon group. Examples include methyl, ethyl, propyl, isopropyl, butyl, and tertiary butyl.

As used herein, the term "alkylene" refers to a bivalent, aliphatic hydrocarbon group. Examples include methylene, ethylene, propylene, isopropylene, butylene, and pentylene.

As used herein, the term "heteroalkylene" refers to an alkylene group where one or more carbon atoms are replaced with an —O—, —S—, or —N(R)— group, where R is hydrogen, a $C_1$-$C_6$ alkyl group, or another substituent group.

As used herein, the term "$C_m$" when used with a group refers to m carbon atoms in that group.

As used herein, the term "carboxyl" refers to —(C=O)—OH.

As used herein, the term "sulfonyl hydroxide" refers to —(SO$_2$)—OH.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a range of about 1 to about 200 should be understood to include the explicitly recited limits of about 1 and about 200, but also to include individual values such as about 2, about 3, and about 4, and sub-ranges such as about 10 to about 50, about 20 to about 100, and so forth. While this disclosure has been described with reference to the specific embodiments thereof, it should be understood by those skilled in the art that various changes may be made and equivalents may be substituted without departing from the true spirit and scope of this disclosure as defined by the appended claims. In addition, many modifications may be made to adapt a particular situation, material, composition of matter, method, operation or operations, to the objective, spirit and scope of this disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of this disclosure. Accordingly, unless specifically indicated herein, the order and grouping of the operations are not a limitation of this disclosure.

What is claimed is:

1. A hydrogel composition comprising:
   a polymer network including a first water-soluble polymer and a second water-soluble polymer that are cross-linked through dynamic bonds; and
   a catalyst to modulate a rate of exchange of crosslinking of the polymer network,
   wherein the catalyst is an N-heterocyclic aromatic compound substituted with an aminoalkyl group and an alkyl sulfonyl hydroxide group.

2. The hydrogel composition of claim 1, wherein the first water-soluble polymer and the second water-soluble polymer are crosslinked through hydrazone bonds.

3. The hydrogel composition of claim 1, wherein the first water-soluble polymer is modified with a hydrazine or hydrazide functional group, and the second water-soluble polymer is modified with an aldehyde functional group.

4. The hydrogel composition of claim 1, wherein the first water-soluble polymer and the second water-soluble polymer are selected from polysaccharides and proteins.

5. The hydrogel composition of claim 1, wherein at least one of the first water-soluble polymer or the second water-soluble polymer is hyaluronic acid.

6. The hydrogel composition of claim 1, wherein the first water-soluble polymer is hyaluronic acid modified with a hydrazine or hydrazide functional group, and the second water-soluble polymer is hyaluronic acid modified with an aldehyde functional group.

7. The hydrogel composition of claim 1, wherein a concentration of the catalyst in the hydrogel composition is in a range from 0.5 mM to 500 mM.

8. The hydrogel composition of claim 1, wherein a content of the polymer network in the hydrogel composition is in a range from 0.5 wt. % to 30 wt. %.

9. A method of therapeutic cell delivery comprising:
providing a first water-soluble polymer and a second water-soluble polymer;
providing a catalyst;
cross-linking the first water-soluble polymer and the second water-soluble polymer through dynamic bonds to form a hydrogel comprising a polymer network;
encapsulating cells in the polymer network of the hydrogel; and
injecting the hydrogel into a subject,
wherein the catalyst facilitates gel shear-thinning and injectability, but quickly diffuses out of the hydrogel after injection, thereby stabilizing the hydrogel and slowing hydrogel erosion after injection to provide a long-term, cell adhesive scaffold for cell culture.

10. The method of claim 9, wherein injecting the hydrogel composition is performed using a syringe.

11. The method of claim 9, wherein the catalyst is a heterocyclic aromatic compound.

12. The method of claim 9, wherein the catalyst is an N-heterocyclic aromatic compound substituted with an amino-containing group and a sulfonyl hydroxide-containing group.

13. The method of claim 9, wherein the catalyst is zwitterionic.

14. A method of forming a hydrogel composition, comprising:
providing a first water-soluble polymer, a second water-soluble polymer, and a catalyst; and
combining the first water-soluble polymer, the second water-soluble polymer, and the catalyst in a liquid medium including water to form the hydrogel composition,
wherein the first water-soluble polymer is modified with a hydrazine or hydrazide functional group, and the second water-soluble polymer is modified with an aldehyde functional group,
wherein the first water-soluble polymer and the second water-soluble polymer are crosslinked through hydrazone bonds to form a polymer network, and a rate of exchange of crosslinking of the polymer network is modulated by the catalyst,
wherein the catalyst is an N-heterocyclic aromatic compound substituted with an aminoalkyl group and an alkyl sulfonyl hydroxide group.

15. The method of claim 14, wherein the first water-soluble polymer and the second water-soluble polymer are selected from polysaccharides and proteins.

16. The method of claim 14, wherein at least one of the first water-soluble polymer or the second water-soluble polymer is hyaluronic acid.

* * * * *